US006783780B1

(12) United States Patent
De Jong et al.

(10) Patent No.: US 6,783,780 B1
(45) Date of Patent: Aug. 31, 2004

(54) PREPARATION THAT CONTAINS OLIGOSACCHARIDES AND PROBIOTICS

(75) Inventors: Patricia De Jong, Maarheeze (NL); Katrien Van Laere, Heteren (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/857,796

(22) PCT Filed: Dec. 9, 1999

(86) PCT No.: PCT/NL99/00755

§ 371 (c)(1),
(2), (4) Date: Jun. 11, 2001

(87) PCT Pub. No.: WO00/33854

PCT Pub. Date: Jun. 13, 2000

(30) Foreign Application Priority Data

Dec. 9, 1998 (NL) .............................. 1010770

(51) Int. Cl.[7] .............................. A23B 7/10; A23B 1/00; A23B 3/00
(52) U.S. Cl. .......................... 426/52; 426/62; 426/656; 424/93.3; 424/93.45
(58) Field of Search .............................. 426/20, 21, 28, 426/31, 44, 52, 62, 656, 658, 615; 435/93, 100, 101, 252.1, 252.9, 255.2; 424/93.45, 93.3

(56) References Cited

U.S. PATENT DOCUMENTS

| 5,021,245 | A | | 6/1991 | Borschel et al. ................ 426/2 |
|---|---|---|---|---|
| 5,700,684 | A | * | 12/1997 | Ehret ....................... 435/255.2 |
| 5,968,569 | A | * | 10/1999 | Cavadini et al. .............. 426/61 |
| 6,203,797 | B1 | * | 3/2001 | Perry ...................... 424/93.45 |
| 6,221,350 | B1 | * | 4/2001 | Brown et al. .............. 424/93.3 |
| 6,254,886 | B1 | * | 7/2001 | Fusca et al. ................. 424/464 |
| 6,284,243 | B1 | * | 9/2001 | Masuyama et al. ....... 424/93.45 |
| 6,403,128 | B2 | * | 6/2002 | Ueda et al. ................... 426/18 |
| 6,461,607 | B1 | * | 10/2002 | Farmer .................... 424/93.45 |

FOREIGN PATENT DOCUMENTS

| EP | 0 856 259 | | 8/1998 |
|---|---|---|---|
| EP | 0 904 784 | | 3/1999 |
| WO | WO 96/26732 | | 9/1996 |
| WO | 97/34615 | * | 9/1997 |
| WO | WO 97/35596 | | 10/1997 |
| WO | WO 98/26787 | | 6/1998 |

* cited by examiner

*Primary Examiner*—Keith Hendricks
(74) *Attorney, Agent, or Firm*—Young & Thompson

(57) ABSTRACT

A preparation having a health-promoting action for the prevention and/or treatment of disorders of the digestive tract, contains one or more probiotics and one or more non-digestible oligosaccharides. The probiotics are preferably chosen from bacterial strains such as a strain of a *Lactobacillus* or a *Bifido bacterium* species and from yeast strains such as a strain of a *Saccharomyces* species.

13 Claims, No Drawings

PREPARATION THAT CONTAINS OLIGOSACCHARIDES AND PROBIOTICS

BACKGROUND OF THE INVENTION

1. Field of the Invention

The present invention relates to a preparation which has a health-promoting action, in particular for the prevention and/or treatment of disorders of the digestive tract, more particularly of the intestines.

The application relates in particular to a preparation of this type which contains probiotics and non-digestible oligosaccharides.

2. Description of the Related Art

It is known that certain microorganisms have both a prophylactic and a therapeutic effect on intestinal diseases, such as intestinal infections. When these microorganisms are administered to humans or animals they will compete with pathogenic bacteria for nutrients and/or adhesion sites on the intestinal wall, as a result of which the number of pathogenic bacteria will decrease and infections are prevented or reduced. Such microorganisms are generally designated by the term "probiotics".

If these microorganisms are to have an optimum action they must reach the intestines alive. A further beneficial effect of the administration of live microorganisms to the intestines is, for example, that they are able to ferment the oligosaccharides present in the intestines, whereby, for example, fatty acids with short chains are formed.

SUMMARY OF THE INVENTION

In addition it is advantageous on economic grounds if as many microorganisms as possible reach the intestines alive. With the customary preparations which contain probiotics the percentage of microorganisms that reaches the intestines alive is frequently low.

It is therefore an object of the present invention to provide a preparation that contains such probiotics with which a high percentage of the microorganisms administered reaches the intestines alive.

It is also an object of the present invention to provide a preparation that can be used for the treatment of disorders of the intestines and/or that can be used for prophylactic treatment of the intestines.

The present invention now relates to a preparation having a health-promoting action, in particular for the prevention and/or treatment of disorders of the digestive tract, more particularly of the intestines, which contains probiotics and non-digestible oligosaccharides.

Without wishing to be tied to any theory, it is assumed that the oligosaccharides form a substrate for the probiotics, as a result of which the likelihood that said microorganisms reach the intestines alive increases and as a result of which the likelihood that they are able, in combination with the oligosaccharides present in the intestines, to exert their beneficial action increases. The oligosaccharides could therefore also be designated as "prebiotics".

DESCRIPTION OF THE PREFERRED EMBODIMENTS

The probiotics and non-digestible oligosaccharides are present in the preparation in a ratio of 1 to 5 g oligosaccharides per $10^8$ to $10^{11}$ cells of the probiotic.

The oligosaccharides used are chosen from the so-called "non-digestible oligosaccharides", that is to say oligosaccharides which are not absorbed by the human or animal body. These oligosaccharides as a rule have a degree of polymerisation of 2 to 20. This implies that the oligosaccharides consist of 2 to 20 monosaccharide units. In the case of a degree of polymerisation of less than 2, that is to say in the case of the monosaccharide, the preparation is not effective since such monosaccharides are absorbed by the human or animal body. At a degree of polymerisation of greater than 20 the oligosaccharides lose their beneficial action.

Preferably the oligosaccharides have a degree of polymerisation of 2 to 10, more preferentially of 2 to 6, more particularly 3 to 10 and more preferentially 3 to 6.

Where reference is made in the present application to oligosaccharides this term is used to refer both to oligosaccharides having one specific chain length and to mixtures of oligosaccharides having different chain lengths. However, a mixture of oligosaccharides having different chain lengths is preferred.

Furthermore, the oligosaccharides usually do not consist entirely of disaccharides. The disaccharide content is usually less than 90% and sometimes less than 60%.

The average degree of polymerisation is as a rule more than 2.1, usually more than 2.5.

The oligosaccharides used in the invention are, as a rule, furthermore so chosen that they are at least 20% usable as substrate for the probiotic microorganisms present in the preparation, as determined by high performance anion exchange chromatography.

Examples of suitable oligosaccharides are transgalacto-oligosaccharides (TOS), fructo-oligosaccharides (FOS) and combinations thereof.

It is particularly advantageous if the oligosaccharides are added to the preparation in the form of a hydrolysis product of one or more polysaccharides, for example chosen from β-(arabino)galactans, β-(arabino)xylans, β-glucans, β-glucomannans, β-galactomannans, α-arabans, inulin and combinations thereof. In addition to the oligosaccharides, such a hydrolysis product can also contains yet further components, such as monosaccharides and saccharides having a degree of polymerisation higher than 20. However, the hydrolysis product must contain at least 50% non-digestible oligosaccharides, preferably at least 70%.

The polysaccharides which are preferably hydrolysed are β-(arabino)galactans, β-mannans, and xylans.

It is also possible to use a hydrolysis product of one or more fibres which are mainly made up of the abovementioned oligosaccharides, such as fibres from oats, wheat, potatoes, sugar beet, soya polysaccharides and the like.

The hydrolysis of the polysaccharide(s) and/or the fibre(s) can be carried out in a manner known per se, for example by the use of suitable enzymes.

The concentration of oligosaccharides in the preparation is such that 0.5 to 20 gram per day can be administered. If desired, this administration can be spread over the day, as long as the total quantity of the oligosaccharides administered remains in the range described above. In general the preparation will be administered 2 to 4 times per day.

In general the oligosaccharides will make up 5 wt. % to 50 wt. % of the total preparation.

The probiotics suitable for the present invention are generally known. They comprise, in general, one or more bacterial strains suitable for use in food preparations, such as lactic acid bacteria suitable for use in food preparations, or one or more yeast strains suitable for use in food preparations, or a combination thereof. These probiotics will usually have GRAS ("Generally Recognised As Safe") status.

Suitable bacterial strains are, for example, chosen from those which are described in EP-A-0 904 784 in the name of the Applicant. Other possible probiotics are the Pediococci, Propionibacteria or Leuconostoc species. The Lactobacillus and Bifidobacterium genera and combinations thereof are to be preferred.

The Bifidobacterium strain used can be any strain which is suitable for, and preferably is also approved for, administration to humans and animals, such as *Bifidobacterium, bifidum, Bifidobacterium breve, Bifidobacterium lactis* or *Bifidobacterium longum*, or a combination thereof.

The Lactobacillus strain is preferably so chosen that this produces mainly, preferably exclusively, dextrorotatary (L+) lactate. What is meant by this is that the lactate produced is less than 5%, preferably less than 2%. laevorotatory lactate. It is, of course, possible that the microorganism produces other metabolites in addition to lactate and the beneficial action of the microorganism can (also) be based on the formation of these further metabolites.

Examples of these are *Lactobacillus acidophilus, Lactobacillus brevis, Lactobacillus (para)casei, Lactobacillus fermentum, Lactobacillus plantarum* and *Lactobacillus rhamnosus*, and combinations thereof.

The yeast strain used in the invention can be any strain which is suitable for, and preferably is also approved for, administration to humans and animals, such as of the genus Saccharomyces. Examples of suitable Saccharomyces species are *Saccharomyces cerevisiae* and *Saccharomyces boulardii*.

The yeast in the preparation can be alive or dead. Both dead and live yeast contains a high content of mannoproteins, which are able to prevent the adhesion of bacteria to the intestinal wall to a large extent. Administration of dead yeast offers advantages in the case of people who are suffering from inflammatory intestinal diseases.

If the yeast is used in dead form, at least one other live microorganism must be used. Said live organism can once again be chosen from both the Lactobacillus, Bifidobacterium, Pediococci, Propionibacteria and Leuconostoc strains, but can also be live Saccharomyces.

It is possible to use both a single microorganism and a mixture of microorganisms.

The total concentration of the probiotics is $10^6$ to $10^{12}$, preferably $10^9$ to $10^{10}$, live cells per gram of total product. If a combination of microorganisms is used, the minimum concentration of each of the microorganisms must be such that there can still be said to be live organisms, that is to say at least approximately 10 per gram of product. The total concentration of microorganisms must always be within the above specified range of $10^6$ to $10^{12}$ live cells per gram of total product.

If dead *Saccharomyces cerevisae* is also used, this is administered in a quantity of 0.5 to 5 g per day.

The combination of *Lactobacillus rhamnosus* with transgalacto-oligosaccharide or hydrolysis products of (potato) galactan is found to be a particularly suitable combination of oligosaccharide and probiotic.

The suitability of a specific oligosaccharide for a specific probiotic can be determined by determining the capacity of the microorganism concerned to ferment said oligosaccharide or said oligosaccharide fraction. A specific method for this is given below with the examples.

The administration forms of the preparations according to the invention are as a rule analogous to those which have been described in EP-A-0 904 784 in the name of the Applicant, the contents of which are incorporated herein by reference. In this context it must be pointed out that according to the present invention also only one probiotic microorganism (including a yeast) can be present and that in addition to the one or more probiotic microorganisms one or more oligosaccharides can also be incorporated, in the quantities specified above.

The preparations according to the present invention can, among others, be administered in the form of a nutritional supplement, total nutrition and clinical nutrition. Reference is likewise made to EP-A-0 904 784 for the specific additives which are added to such foods and the preparation and applications of such foods.

The probiotics are preferably added to the preparation in (freeze-)dried form. It is also possible to produce liquid preparations, but these must be stored cool. Furthermore, one or more of the microorganisms can be used in encapsulated form, for example in order to improve the shelf life.

If the preparation according to the invention is used as a nutritional supplement, it can be administered as such, can be mixed with a suitable drinkable liquid, such as water, yoghurt, milk or fruit juice, or can be mixed with solid or liquid food. In this context the nutritional supplement can be in the form of tablets, capsules, powders, sachets, pastilles, sweets, bars and corresponding administration forms, usually in the form of a unit dose.

A supplement according to the invention can, for example, have the following composition:

| | |
|---|---|
| probiotics: | 10–40 wt. % |
| oligosaccharides: | 40–80 wt. % |
| further additives: | 0–40 wt. %, |

The preparation can also be in the form of a food preparation that is suitable for direct consumption, such as total or clinical nutrition. This can be either oral nutrition or nutrition for administration via a tube or catheter.

Such foods can be in solid form or liquid/drinkable form and can contain all customary additives for (total and/or clinical) nutrition, including proteins, vitamins, minerals, trace elements and the like.

A total nutrition according to the invention can, for example, have the following composition:

| | |
|---|---|
| probiotics: | 0.1–10 wt. % |
| oligosaccharides: | 1–20 wt. % |
| further additives: | 75–95 wt. %, | further additives: 75–95 wt. %
to a total of 100 wt. %.

According to a particular embodiment, the preparation according to the invention is in the form of a (supplement for a) baby food or a nutritional supplement for babies.

The preparations described above can be used for the same applications as those described in EP-A-0 904 784 in the name of the Applicant, in particular in the treatment of disorders of the intestines, such as diarrhea, such as can arise when travelling or after treatment with antibiotics, or which results from food poisoning. Another application is in the treatment of inflammatory bowel diseases (IBD), such as colitis ulcerosa and Crohn's disease. The preparations according to the invention are also suitable for patients who have a food allergy, such as an allergy to cow's milk or to gluten.

The probiotics and non-digestible oligosaccharides can also be used in baby food to prevent or treat intestinal problems.

The invention will now be explained with the aid of the following non-limiting examples.

EXAMPLES

To determine suitable combinations of oligosaccharides and probiotics the microorganisms listed below were tested to determine their capacity to ferment structurally different oligosaccharide fractions. Strains pre-cultured in liquid medium based on thioglycolate (Oxoid, Unipath Ltd, Basingstoke, Hampshire, UK) were subjected to sub-culture in thioglycolate to which 0.5% (m/V) oligosaccharides were added. The sugar-free thioglycolate medium and the oligosaccharide solutions were sterilised separately for 15 minutes at 121° C.

Following anaerobic incubation for 48 hours at 37° C. the pH was measured with the aid of a micro-pH meter (Sentron, Roden, The Netherlands). The changes in the residual oligosaccharide content and the formation of reaction products were determined using HPAEC (high performance anionic exchange chromatography). For HPAEC analysis the cultures were centrifuged and the supematant liquor was diluted 10-fold with $H_2O$ and boiled for 5 minutes to stop the enzymatic activity. The purity of the stains was checked before and after fermentation.

The HPAEC system consisted of a Dionex Bio-LC GPM-II quaternary gradient module (Dionex Corporation. Sunnyval, Calif., USA) equipped with a Dionex Carbopac PA-100 column (4*250 mm) in combination with a Carbopac PA-100 guard column (3*25 mm). The samples (20 $\mu$l) were injected using a Spectra Physics SP8880 autosampler. The oligomers were analysed using a gradient of sodium acetate in 100 mmol.l$^{-1}$ NaOH.

The results of these experiments are given below in the table for a number of combinations of probiotics and substrates, where:

| Bacteria | Substrate Hydrolysis product of: | | | |
|---|---|---|---|---|
| | Arabino-galactans | Arabans | Arabinoxylans | Fructans |
| Bi. Breve | ++ | + | − | ++ |
| Bi. Longum | ++ | ++ | + | ++ |
| Bi. adolescentis | ++ | + | ++ | ++ |
| L. acidophilus | ++ | − | − | + |
| L. fermentum | ++ | − | − | + |
| K. pnuemoniae | ++ | − | − | + |
| C. perfingens | − | − | − | ++ |

A few examples of preparations according to the present invention are given below.

Example I

Supplement

A suspension of *Lactobacillus rhamnosus* ATCC 7469 (Lb) was freeze-dried, a powder being obtained which contained at least $10^9$ viable cells per gram powder. Transgalacto-oligosaccharides (TOS), obtained from lactose (Borculo Whey Products), were dissolved in water at 40° C. to a solids content of 25% and this solution was spray-dried. The two powders were mixed in a TOS/Lb ratio of 4/1 until a homogeneous product was obtained. Sachets were filled with 2–5 g of this mixture, depending on the dosage regime (5 g for one sachet per day; 3 g for two sachets per day). The contents of one sachet can, for example, be taken mixed in a glass of orange juice or milk.

Example II

Synbiotic Bar

A 23 g bar was prepared from 4.0 g oat flakes, 4.0 g wheat flakes, 3.0 g puffed rice, 1.0 g crushed hazelnuts, 0.25 g honey, 3.0 g raisins, 1.5 g maltodextrin, 1.0 g freeze-dried *Lb rhamnosus*, 0.5 g baker's yeast (*Saccharomyces cerevisiae*; Gist Brocades) and 5.0 g transgalacto-oligosaccharides.

Example III

Method for Hydrolysing Vegetable Fibres

A 20% suspension of fibres, for example from wheat, potatoes, oats, soya polysaccharides, carob gum or sugar beet, in water was prepared. These sources of fibre are commercially available. The suspension was heated to a temperature of between 20 and 50° C. (preferably 35–45° C.), after which enzymes were added in a quantity of one part enzyme per 5–500 parts (m/m) substrate. The choice of the type of enzyme is dependent on the type of polysaccharide. Examples of suitable enzymes are Novoferm Pectinex Ultra s.p.-L, Pentopan and Ultra.s.p. (NOVO).

After 0.5–4 hours the reaction was terminated by heating, after which the solution thus obtained can be used as the oligosaccharide fraction in the preparations according to the invention, optionally after further filtration/purification or after concentrating.

Example IV

Synbiotic Mixture for Mixing with a Complete Enteral Clinical Nutrition

A mother batch of a powder mixture was prepared in accordance with the method of Example I. The powder consisted of 20% hydrolysed wheat arabinoxylans, 20% hydrolysed potato arabinogalactans, 20% hydrolysed carob gum, 20% hydrolysed sugar beet fibre (arabans), 15% hydrolysed oat fibres (glucans) and 5% *Bifidobacterium longum*. 5 g of the powder mixture is placed in a sachet. The contents of this sachet can be added to a standard enteral clinical nutrition a maximum of 30 min before use.

Example V

Synbiotic Powder Mixture for Fortifying Baby Food

A synbiotic mixture was prepared in accordance with the method of Example I. The composition contains 10% bakers yeast (Gist Brocades), 40% mannoproteins, obtained from yeast, 25% inulin and 25% raffinose.

Example VI

Sweet that Contains a Synbiotic Mixture

A 2 g sweet was prepared starting from 58% digestible carbohydrates (glucose Syrup), 35% TOS, 4% *Lactobacillus rhamnosus* ATCC 7469, and 2% flavourings and colourants.

What is claimed is:

1. A nutritional supplement for the prevention and/or treatment of disorders of the digestive tract, which comprises probiotics comprising a bacterial strain selected from the group consisting of *Lactobacillus, Bifidobacterium* and *Propionibacterium* strains and at least one yeast strain and 40–80 weight % of one or more oligosaccharides that are non-digestible by humans, said supplement being in dried form.

2. The supplement according to claim 1, wherein the one or more oligosaccharides have a degree of polymerization of 2 to 20.

3. The supplement according to claim 2, wherein the oligosaccharides have a degree of polymerization of 2 to 10.

4. The supplement according to claim 2, wherein the oligosaccharides have a degree of polymerization of 2 to 6.

5. The supplement according to claim 1, wherein the one or more oligosaccharides have been obtained by the hydrolysis of one or more polysaccharides selected from the group consisting of β-(arabino)galactans, β-(arabino)xylans, β-glucans, β-glucomannans, β-galactomannans, α-arabans, inulin and combinations thereof.

6. The supplement according to claim 2, wherein the oligosaccharides have been obtained by the hydrolysis of one or more polysaccharides selected from the group consisting of β-(arabino)galactans, β-(arabino)xylans, β-glucans, β-glucomannans, β-galactomannans, α-arabans, inulin and combinations thereof.

7. The supplement according to claim 5, wherein the one or more polysaccharides are selected from the group consisting of β-(arabino)galactans, β-glucomannans, β-(arabino)xylans and combinations thereof.

8. The supplement according to claim 1, wherein the oligosaccharides are produced by hydrolysis of one or more fibers originating from oats, wheat, potatoes, sugar beet, and soya polysaccharides.

9. The supplement according to claim 2, wherein the oligosaccharides are produced by hydrolysis of one or more fibers originating from oats, wheat, potatoes, sugar beet, and soya polysaccharide.

10. The supplement according to claim 1, further comprising dead yeast cells.

11. The supplement according to claim 1, wherein the ratio between the probiotics and the one or more non-digestible oligosaccharides is in the range of 1 to 5 g oligosaccharides per $10^8$ to $10^{11}$ cells of the probiotics.

12. The supplement according to claim 1, which contains the probiotics in a concentration of $10^7$ to $10^{11}$ live cells per gram of total product.

13. A nutritional supplement for the prevention and/or treatment of disorders of the digestive tract, which comprises probiotics comprising a lactic acid bacterial strain and a yeast strain of a *Saccharomyces* species and 40–80 weight % of one or more oligo-saccharides that are non-digestible by humans, said supplement being in dried form.

* * * * *